US005780238A

United States Patent [19]
Weiner et al.

[11] Patent Number: 5,780,238
[45] Date of Patent: *Jul. 14, 1998

[54] VPR RECEPTOR PROTEIN

[75] Inventors: David B. Weiner, Merion, Pa.; David Nathan Levy; Yosef Refaeli, both of Boston, Mass.

[73] Assignee: The Trustees of the University of Pennsylvania, Philadelphia, Pa.

[*] Notice: The term of this patent shall not extend beyond the expiration date of Pat. No. 5,639,598.

[21] Appl. No.: 652,572

[22] PCT Filed: Dec. 15, 1994

[86] PCT No.: PCT/US94/14532

§ 371 Date: Oct. 24, 1996

§ 102(e) Date: Oct. 24, 1996

[87] PCT Pub. No.: WO95/16705

PCT Pub. Date: Jun. 22, 1995

Related U.S. Application Data

[63] Continuation-in-part of Ser. No. 167,519, Dec. 15, 1993, abandoned.

[51] Int. Cl.$^6$ .................... G01N 33/566; C07K 14/705; C07K 14/47
[52] U.S. Cl. .................. 435/7.1; 435/5; 435/7.2; 436/501; 530/350; 530/300
[58] Field of Search .................. 530/350, 300; 436/501; 435/7.2, 5, 7.1

[56] References Cited

U.S. PATENT DOCUMENTS

| | | | |
|---|---|---|---|
| 5,001,230 | 3/1991 | Brown et al. | 536/27 |
| 5,593,972 | 1/1997 | Weiner et al. | 514/44 |
| 5,639,598 | 6/1997 | Weiner et al. | 435/5 |

FOREIGN PATENT DOCUMENTS 9531901   11/1995   WIPO .

OTHER PUBLICATIONS

Refaeli et al., The glucocorticoid receptor type II complex is a target of the HIV-1 vpr gene product, PNAS, 92(8): 3621-3625., Apr. 1995.
Goudsmit et al., Map of sequential B cell epitopes of the HIV-1 transmembrane protein using human antibodies as probe, Intervirology, 31(6): 327-338., Jun. 1990.
Adachi et al., "Production of Acquired Immunodeficiency Syndrome-Associated Retrovirus in Human and Nonhuman Cells Transfected With an Infectious Molecular Clone", *J. of Virology* 1986, 59, 284-291.
Aguanno et al., "12-O-Tetradecanoylphorbol-13-Acetate–Induced Differentiation of a Human Rhabdomyosarcoma Cell Line", *Cancer Research*, vol. 50, 3377-3382.
Arya et al., "Trans-Activator Gene of Human T-Lymphotropic Virus Type III (HTLV-III)", *Science* 1985, 229, 69-73.

Chantal Petit et al., "Human Immunodeficiency Virus Infection Down-Regualtes HLA Class II Expression and Induces Differentiation in Promonocytic U937 Cells", *J. Clin. Invest.* 1987, 79, 1883-1889.
Cohen et al., "Identification of HIV-1 vpr Product and Function", *J. Acquir. Immune Defic. Syndr.* 1990, 3, 11-18.
Cohen et al., "Human Immunodeficiency Virus vpr Product Is a Virion-Associated Regulatory Protein", *J. Virol.* 1990, 64, 3097-3099.
Colmenares et al., "The ski Oncogene Induces Muscle Differentiation in Quail Embryo Cells", *Cell* 1989, 59, 293-303.
Dedera et al., "Viral Protein R of Human Immunodeficiency Virus Types 1 and 2 IS Dispensable for Replication and Cytopathogenicity in Lymphoid Cells", *J. of Virol.* 1989, 63, 3205-3208.
Fisher et al., "A Molecular Clone of HTLV-III With Biological Activity", *Nature* 1985, 316, 262-265.
Gallo et al., "Frequent Detection and Isolation of Cytopathic Retroviruses (HTLV-III) from Patients with AIDS and at Risk for AIDS", *Science* 1984, 224, 500-503.
Garrett et al., "Rev Activates Expression of the Human Immunodeficiency Virus Type 1 vif and vpr Gene Products", *J. of Virology*, vol. 65, 1653-1657.
Gras-Masse et al., "A Synthetic Protein Corresponding to the Entire vpr gene Product from the Human Immunodeficiency Virus HIV-1 is Recognized by Antibodies From HIV-Infected Patients", *Int. J. Peptide protein Res.* 1990, 36, 219-226.
Harada et al., "Tumor Promoter, TPA, Enhances Replication of HTLV-III/LAV", *Virology* 1986, 154, 249-258.
Hattori et al., "The Human Immunodeficiency Virus Type 2 vpr Gene is Essential for Productive Infection of Human Macrophages", *PNAS USA* 1990, 87, 8080-8084.
Hiti et al., "Expression of the MyoD1 Muscle Determination Gene Defines Differentiation Capability but Not Tumorigenicity of Human Rhabdomyosarcomas", *Mol. Cell. Biol.* 1989, 9, 4722-4730.
Kozak, M., "Point Mutations Define a Sequence Flanking the AUG Initiator Codon That Modulates Translation by Eukaryotic Ribosomes", *Cell* 1986, 44, 283-292.
Levy et al, "Isolation of Lymphocytopathic Retroviruses from San Francisco Patients with AIDS", *Science* 1984, 225, 840-842.

(List continued on next page.)

Primary Examiner—Stephen Walsh
Assistant Examiner—Claire M. Kaufman
Attorney, Agent, or Firm—Woodcock Washburn Kurtz Mackiewicz & Norris, LLP

[57] ABSTRACT

A human receptor protein which binds to the human immunodeficiency virus (HIV) viral protein R (vpr) is disclosed. Pharmaceutical compositions that comprise the receptor protein, compositions useful to produce the receptor protein and methods of making and using the receptor protein are disclosed.

5 Claims, No Drawings

OTHER PUBLICATIONS

Levy et al., "Induction of Cell Differentiation by Human Immunodeficiency Virus 1 vpr", *Cell* 1993, 72, 541–550.

Li et al., "Human Immunodeficiency Virus Type 1 DNA Synthesis, Integration, and Efficient Viral Replication in Growth–Arrested T Cells", *J. Virol.* 1993, 67, 3969–3977.

Ling et al., "Optimization of the Polymerase Chain Reaction with Regard to Fidelity: Modified T7, Taq and Vent DNA Polymerases", *PCR Meth. Appl.* 1991, 1, 63–69.

Morgenstern et al., "Advanced Mammalian Gene Transfer: High Titre Retroviral Vectors with Multiple Drug Selection Markers and a Complementary Helper–Free Packaging Cell Line", *Nucl. Acids Res.* 1990, 18, 3587–3596.

Myers et al., "The Emergence of Simian–Human Immunodeficiency Viruses", *AIDS Res. Hum. Retrovir.* 1992, 8, 373–386.

Ogawa et al., "Mutational Analysis of the Human Immunodeficiency Virus vpr Open Reading Frame", *J. Virol.* 1989, 63, 4110–4114.

Ratner et al., "Complete Nucleotide Sequence of the AIDS Virus, HTLV–III", *Nature* 1985, 313, 277–284.

Ratner et al., "Complete Nucleotide Sequences of Functional Clones of the AIDS Virus", *AIDS Res. Hum. Retroviruses* 1987, 3, 57–69.

Reiss et al., "Antibody Response to Viral Proteins U (vpu) and R (vpr) in HIV–1 Infected Individuals", *J. of Aquired Immune Deficiency Syndromes* 1990, 3, 115–122.

Korber et al., "Signature Pattern Analysis: A Method for Assessing Viral Sequence Relatedness", *AIDS Res. Human Retro.* 1992, 8, 1549–1560.

Rich et al., "Increased Susceptibility of Differentiated Mononuclear Phagocytes to Productive Infection with Human Immunodeficiency Virus–1 (HIV–1)", *J. Clin. Invest.* 1992, 89, 176–183.

Rose et al., "Frequent Identification of HIV–1 DNA in Bronchoalveolar Lavage Cells Obtained from Individuals with the Aquired Immunodeficiency Syndrome[1-3]", *Am. Rev. Respir. Dis.* 1986, 143, 850–854.

Roulston et al., "Induction of Monocytic Differentiation and NF–kB–like Activities by Human Immunodeficiency Virus 1 Infection of Myelomonoblastic Cells", *J. Exp. Med.* 1992, 175, 751–763.

Salahuddin et al., "Human T Lymphotropic Virus Type III Infection of Human Alveolar Macrophages", *Blood* 1986, 68, 281–284.

Sato, A. et al., "Identification and Localization of vpr Gene Product of Human Immunodeficiency Virus Type 1", *Virus Genes* 1990, 4(4), 303–312.

Schuitemaker et al., "Biological Phenotype of Human Immunodeficiency Vorus Type 1 Clones at Different Stages of Infection: Progression of Disease is Associated with a Shift from Monocytotrophic to T–Cell–Tropic Virus Populations", *J. Virol.* 1992, 66, 1354–1360.

Shibata et al., "Mutational Analysis of Simian Immunodeficiency Virus From African Green Monkeys and Human Immunodeficiency Virus Type 2", *J. Med. Primatol.* 1990, 19, 217–225.

Shibata et al., "Mutational Analysis of the Human Immunodeficiency Virus Type 2 (HIV–2) Genome in Relation to HIV–1 and Simian Immunodeficiency Virus $SIV_{AGM}$", *J. Virol.* 1990, 64, 742–747.

Siegel et al., "Morphological and Biochemical Differentiation of the Human Medulloblastoma Cell Line TE671", *Dev. Brain Res.* 1988, 44, 269–280.

Starcich et al., "Characterization of Long Terminal Repeat Sequences of HTLV–III", *Science* 1985, 227, 538–540.

Stratton et al., "Characterization of the Human Cell Line TE671", *Carcinogenesis* 1989, 10, 899–905.

Valentin et al., "In Vitro Maturation of Mononuclear Phagocytes and Susceptibility to HIV–1 Infection", *J. of Acq. Imm. Def. Synd.* 1991, 4, 751–759.

Weiner et al., "Human Genes Other than CD4 Facilitate HIV–1 Infection of Murine Cells", *Pathobiology* 1991, 59, 361–371.

Weiner et al., "Linkage of Tyrosine Kinase Activity with Transforming Ability of the p185neu Oncoprotein", *Oncogene* 1989 4, 1175–1183.

Westervelt et al., "Dual Regulation of Silent and Productive Infection in Monocytes by Distinct Human Immunodeficiency Virus Type 1 Determinants", *J. Virol.* 1992, 66, 3925–3931.

Wong–Staal et al., "Human Immunodeficiency Virus: The Eighth Gene", *AIDS Res. Hum. Retroviruses* 1987, 3, 33–39.

Yu et al., "Open Reading Frame vpr of Simian Immunodeficiency Virus Encodes a Virion–Associated Protein", *J. Virol.* 1990, 64m 5688–5693.

Yuan et al., "Human Immunodeficiency Virus vpr Gene Encodes a Virion–Associated Protein", *AIDS Res. Hum. Retroviruses* 1990, 6, 1265–1271.

Zack et al., "HIV–1 Production from Infected Peripheral Blood T Cells After HTLV–1 Induced Mitogenic Stimulation", *Science* 240, 1026–1029.

Janel et al., "Localization of the vpr Gene Product in SIVmac Infected Cells", *International Conference on AIDS* Jun.1989, 5, p. 523, Abstract T.C.O. 45.

Refaeli et al., "Recombinant HIV–1 Vpr Protein Induces Cellular Differentiation in Vitro", *J. of Cellular Biochemistry*, Supplement 18B, 1994, p. 140, abstract J 262.

VPR RECEPTOR PROTEIN

This application is a National Stage application of PCT/US94/14532, filed under 35 U.S.C. §371 on Dec. 15, 1994, which is a continuation-in-part application of Ser. No. 08/167,519, filed Dec. 15, 1993, now abandoned.

FIELD OF THE INVENTION

The present invention relates to a human receptor protein which binds to the human immunodeficiency virus (HIV) viral protein R (vpr), to pharmaceutical compositions that comprise the receptor protein, to compositions useful to produce the receptor protein and to methods of making and using the receptor protein. The present invention is related to U.S. application Ser. No. 08/167,519 filed Dec. 15, 1993, which is incorporated herein by reference.

BACKGROUND OF THE INVENTION

Since the demonstration in 1987 that the small open reading frame within HIV-1 designated R encodes a 15 kd protein (Wong-Staal, F., et al., (1987) *AIDS Res. Hum. Retroviruses* 3:33–39), relatively little regarding the function of the viral protein R (vpr) has been reported. The vpr open reading frame is conserved within all genomes of HIV-1 and HIV-2 and within most, if not all, simian immunodeficiency virus (SIV) genomes. VPR is immunogenic in vivo in that a large subset of HIV individuals makes antibodies that can react with a bacterially produced vpr peptide (Wong-Staal, F., et al., (1987) *AIDS Res. Hum. Retroviruses* 3:33–39).

The progression from HIV infection to AIDS is in large part determined by the effects of HIV on the cells that it infects, including CD4+ T lymphocytes and macrophages. On the other hand, cell activation, differentiation and proliferation are in turn thought to regulate HIV infection and replication in T cells and macrophages. Gallo, R. C. et al. (1984) *Science* 224:500; Levy, J. A. et al., (1984) *Science* 225:840; Zack, J. A. et al. (1988) *Science* 240:1026; Griffin, G. E. et al., (1988) *Nature* 339:70; Valentin, A. et al. (1991) *J. AIDS* 4:751; Rich, E. A. et al., (1992) *J. Clin. Invest.* 89:176; and Schuitemaker, H. et al. (1992) *J. Virol.* 66:1354. Cell division per se may not be required since HIV and other lentiviruses can proliferate in nonproliferating, terminally differentiated macrophages and growth-arrested T lymphocytes. Rose, R. M. et al. (1986) *Am. Rev. Respir. Dis.* 143:850; Salahuddin, S. Z. et al. (1986) *Blood* 68:281; and Li, G. et al. (1993) *J. Virol.* 67:3969. The ability of lentiviruses, including HIV, to replicate in nonproliferating cells, particularly in macrophages, is believed to be unique among retroviruses and it may be significant that several lentiviruses contain a vpr-like gene. Myers, G. et al. (1992) *AIDS Res. Hum. Retrovir.* 8:373. HIV infection of myeloid cell lines can result in a more differentiated phenotype and increase the expression of factors such as NF-KB which are necessary for HIV replication. Roulston, A. et al. (1992) *J. Exp. Med.* 175:751; and Chantal Petit, A. J. et al. (1987) *J. Clin. Invest.* 79:1883.

The most evidence for the function of the vpr protein comes from several studies reporting the activities of HIV strains that have mutations in the vpr gene. It has been reported that mutations in the vpr gene results in a decrease in the replication and cytopathogenicity of HIV-1, HIV-2, and SIV in primary CD4+T lymphocytes and transformed T cell lines (Ogawa, K., et al., (1989) *J. Virol.* 63:4110–4114; Shibata, R., et al. (1990a). *J. Med. Primatol.* 19:217–225; Shibata, R., et al. (1990b) *J. Virol.* 64:742–747 and Westervelt, P. et al. (1992) *J. Virol.* 66:3925), although others have reported mutated vpr gene had no effect on replication (Dedera, D., et al. (1989) *Virol.* 63:3205–3208). Interestingly HIV-2 mutated for vpr has been reported unable to infect primary monocyte/macrophages (Hattori, N., et al. (1990) *Proc. Natl. Acad. Sci. U.S.A.* 87:8080–8084). Transactivation of the HIV long terminal repeat and heterologous promoters by HIV is increased about 3-fold in wild-type versus vpr-negative HIV-1, though the mechanism through which vpr may transactivate transcription is unknown and may be indirect (Cohen, E. A., et al., (1990b) *J. Acquir. Immune Defic. Syndr.* 3:11–18). The relationship between the effects of vpr on promoter activity and viral infectivity is not clear. Vpr protein is incorporated into the viral particle, and this finding has led to the proposition that vpr functions early in infection, following virus penetration and uncoating, and that vpr may interact with cellular regulatory mechanisms important in the establishment of infection (Cohen, E. A., et al. 1990a *J. Virol.* 64:3097–3099; Yu, X. F., et al. (1990) *J. Virol.* 64:5688–5693.; and, Yuan, X., et al., (1990) *AIDS Res. Hum. Retroviruses* 6:1265–1271).

The vpr gene of HIV-1 has been shown to induce cellular growth inhibition and differentiation in tumor lines of intermediate differentiation in vitro. Levy, D. N. et al. (1993) *Cell* 72:541. Since vpr protein originates within viral particles, vpr may play a role in establishing productive infection.

There is a need to understand the activity of vpr and its role in HIV infection at the molecular and cellular level. There is a need to identify the cellular proteins that bind to vpr. There is a need to identify molecules that inhibit vpr activity. There is a need for anti-HIV therapeutics and protective agents.

SUMMARY OF THE INVENTION

The present invention relates to essentially pure human protein which is the receptor of HIV vpr, that is it binds to vpr. The protein when unbound to vpr occurs in the cytoplasm of human cells and is transported from the cytoplasm to the nucleus when bound to vpr. The protein has an apparent molecular weight of between 40–43 kD. Using 12% matrices in SDS-PAGE, the observed molecular weight of the protein is 41 kD. The protein binds to human glucocorticoid receptor protein. The present invention relates to compositions having about 95% pure vpr receptor protein.

The present invention relates to fragments of the vpr receptor which bind to vpr.

The present invention relates to a method of identifying compounds which inhibit vpr protein binding to the vpr receptor protein that comprises the steps of first contacting vpr protein and the vpr receptor protein or a fragment thereof which binds to vpr in the presence of a test compound, then determining the level of binding band then comparing that level to the level of binding that occurs when vpr protein and the vpr receptor protein are contacted in the absence of a test compound.

The present invention relates to a kit for identifying compounds which inhibit vpr protein binding to the vpr receptor protein which comprises a first container comprising vpr protein and a second container comprising the vpr receptor protein or a fragment thereof which binds to vpr.

The present invention relates to antibodies that specifically bind to the vpr receptor protein.

The present invention relates to pharmaceutical compositions that comprise the vpr receptor protein or a fragment thereof which binds to vpr, and a pharmaceutically acceptable carrier.

The present invention relates to a method of treating an individual exposed to HIV by administering the vpr receptor protein.

DESCRIPTION OF PREFERRED EMBODIMENTS OF THE INVENTION

The present invention arises out of the discovery that HIV regulatory protein vpr (referred to herein as "vpr" or "vpr protein") binds to protein found in the cytoplasm of human cells. The human protein, referred to herein as "vpr receptor protein", has an apparent molecular weight of between 40–43 kD. The vpr receptor protein has been observed to have a molecular weight of about 41 kD as determined using 12% SDS-PAGE. The vpr receptor protein has the ability to bind to vpr. The vpr receptor protein has the ability to bind to the human glucocorticoid receptor. The vpr receptor protein is soluble in Triton. It has been discovered that when vpr binds to the vpr receptor protein in cells, the vpr receptor protein which is normally found in the cytoplasm of human cells and the vpr protein bound to it are transported from the cytoplasm to the nucleus. The vpr receptor protein is colocalized with the T-cell and B-cell transcription factor NFkB.

As described in U.S. patent application Ser. No. 08/019,601 filed Feb. 19, 1993 entitled VPR Function and Activity and the U.S. Patent Application filed herewith which is entitled VPR Function and Activity and which is a continuation in part of U.S. patent application Ser. No. 08/167,519, both of which are incorporated herein by reference, vpr has several activities which are involved in HIV infection. In particular, vpr is believed to enhance retroviral infection by causing changes in cells that make them better hosts for HIV replication.

The discovery of the vpr receptor protein in human cells and its transport from cytoplasm to the nucleus when bound to vpr indicate that the binding of vpr to the human receptor protein is involved in HIV replication and thus pathogenesis. Accordingly, the inhibition of such interaction effectively inactivates vpr and prevents it from converting cells to better HIV replication hosts.

The present invention relates to essentially pure human vpr receptor protein. The vpr receptor protein can be isolated from human cells by passing a human cell preparation through an immobilized vpr column under conditions which allow vpr/vpr receptor binding and then changing the conditions to those which do not favor such binding. The released vpr receptor can be collected in essentially pure form. Further purification may be achieved using routine chromatography means.

The following procedure may be used to purify vpr receptor proteins. Cell extracts from primary T cells and monocytes as well as peripheral blood cells and macrophages are obtained by methods known to those skilled in the art. Cell extracts are separated by affinity chromatography. Briefly, eukaryotically-produced vpr is immobilized to a solid support matrix via one or more covalent bonds. Solid support matrices include agarose, polyacrylamide-agarose, controlled-pore glass and other such materials known to those skilled in the art. One skilled in the art will readily appreciate the standard techniques involved in coupling vpr to the matrix as well as techniques involved in activation of the matrix. A spacer molecule may be employed to distance vpr from the matrix backbone in order to allow vpr to more freely bind proteins in the cell extract. One skilled in the art will readily appreciate the variety of spacer molecules with which to use.

The cell extract is layered onto the vpr affinity column by standard methods known to those skilled in the art. Appropriate buffers, washing conditions and elution conditions, which are known to those skilled in the art, are chosen. The resulting eluate may be further purified to homogeneity by techniques such high performance liquid chromatography (HPLC) or other such methods as known to those skilled in the art.

The vpr receptor protein has been purified to approximately 95% purity by a vpr-affinity column using this technique of purification. The protein has a molecular weight of about 40–43 kDa when separated by reducing SDS-PAGE. Using SDS-PAGE with a 12% electrophoresis matrix, the vpr receptor was observed to migrate with a molecular weight of 41 kD. The protein has been detected in rhabdomyosarcoma cell lines TE 671 and RD; osteosarcoma cell lines D17 and HOS; glioblastoma cell lines HTB14, U373 and HBT10; as well as T-cell lines Supt-1 and H9 and monocyte/macrophage lines U937, THP-1, KG-1 and HL-60 as well as primary cells.

Techniques for the cloning of a protein are widely known to those skilled in the art. Briefly, a pure preparation of the 41 kDa cellular protein that binds vpr is sequenced by standard N-terminal sequencing techniques known to those skilled in the art. A set of oligonucleotide probes coding for the deduced amino acid sequence of the N-terminal portion of the 41 kDa protein is designed by techniques known to those skilled in the art. This set of probes is used to screen a human CDNA library by techniques known to those skilled in the art. Positive plaques are selected and sequenced by methods such as dideoxy sequencing for the entire nucleotide sequence of the 41 kDa protein.

Alternatively, a pure preparation of the 41 kDa protein may be injected into a mammal, such as a rabbit, resulting in the production of a polyclonal antiserum. Such immunization procedures are well known to those skilled in the art. In addition, plasma cells (antibody-producing B cells) may be isolated from the injected mammal and fused with myeloma cells to produce hybridomas which produce monoclonal antibodies. Such methods are well known to those skilled in the art. The polyclonal antiserum may be used to screen a human cDNA expression library wherein cells expressing the 41 kDa protein may be identified with the antiserum. Positive clones are selected and the DNA isolated and sequenced by methods known to those skilled in the art.

Once the complete nucleotide sequence of the 41 kDa cellular protein is known, the sequence, or any portion thereof, can be incorporated into a plasmid vector or any other vector capable of expressing the 41 kDa protein. In addition, mammalian cells as well as bacterial cells may be transformed with the plasmid construct containing the sequence, or derivatives thereof, encoding the 41 kDa protein. Said transformed cells may produce the 41 kDa protein intracellularly or extracellularly. In addition, oligonucleotides corresponding to the portions of the sense or antisense of the 41 kDa protein may also be produced. These oligonucleotides may comprises between 10 and 5000 nucleotides, preferably between 10 and 500 nucleotides, most preferably between 10 and 100 nucleotides.

The present invention also relates to: a nucleic acid molecule that comprises a nucleotide sequence that encodes vpr receptor protein or a fragment thereof; an expression vector that comprises a nucleotide sequence that encodes vpr receptor protein or a fragment thereof; a host cell which comprises the expression vector; and a method of producing a vpr receptor protein or a fragment thereof comprising the step of culturing the host cell.

Vpr receptor protein may be produced by routine means using readily available starting materials as described above.

Provision of a suitable DNA sequence encoding the desired protein permits the production of the protein using recombinant techniques now known in the art. The DNA sequence may also be obtained from other sources of HIV DNA or can be prepared chemically using a synthesized nucleotide sequence. When the coding DNA is prepared synthetically, advantage can be taken of known codon preferences of the intended host where the DNA is to be expressed.

One having ordinary skill in the art can, using well known techniques, obtain a DNA molecule encoding the vpr receptor protein and insert that DNA molecule into a commercially available expression vector for use in well known expression systems. For example, the commercially available plasmid pSE420 (Invitrogen, San Diego, Calif.) may be used for production in *E. coli*. The commercially available plasmid pYES2 (Invitrogen, San Diego, Calif.) may be used for production in *S. cerevisiae* strains of yeast. The commercially available MaxBac™ (Invitrogen, San Diego, Calif.) complete baculovirus expression system may be used for production in insect cells. The commercially available plasmid pcDNA I (Invitrogen, San Diego, Calif.) may be used for production in may be used for production in mammalian cells such as Chinese Hamster Ovary cells. One having ordinary skill in the art can use these commercial expression vectors systems or others to produce vpr receptor protein using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate the vpr receptor protein or fragments thereof produced using such expression systems.

In addition to isolating vpr receptor protein from natural sources and producing vpr receptor protein or fragments thereof by recombinant techniques, automated amino acid synthesizers may also be employed to produce vpr receptor protein or fragments thereof. It should be further noted that if the proteins herein are made synthetically, substitution by amino acids which are not encoded by the gene may also be made. Alternative residues include, for example, the ω amino acids of the formula $H_2N(CH_2)_nCOOH$ wherein n is 2–6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

The pharmaceutical composition comprising vpr receptor protein or a fragment thereof and a pharmaceutically acceptable carrier or diluent may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field.

For parenteral administration, the vpr receptor protein or a fragment thereof can be, for example, formulated as a solution, suspension, emulsion or lyophilized powder in association with a pharmaceutically acceptable parenteral vehicle. Examples of such vehicles are water, saline, Ringer's solution, dextrose solution, and 5' human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions comprising vpr receptor protein, or fragments or derivatives may be administered by any means that enables the active agent to reach the agent's site of. action in the body of a mammal. The dosage administered varies depending upon factors such as: pharmacodynamic characteristics; its mode and route of administration; age, health, and weight of the recipient; nature and extent of symptoms; kind of concurrent-treatment; and frequency of treatment. Usually, a daily dosage of vpr receptor protein can be about 1 µg to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Another aspect of the present invention relates to pharmaceutical compositions that comprise a nucleic acid molecule that encodes vpr receptor protein or a fragment thereof and a pharmaceutically acceptable carrier or diluent. According to the present invention, genetic material that encodes vpr receptor protein or a fragment thereof is delivered to an individual in an expressible form. The genetic material, DNA or RNA, is taken up by the cells of the individual and expressed. Pharmaceutical compositions comprising genetic material that encodes vpr receptor protein are useful in the same manner as pharmaceutical compositions comprising vpr receptor protein.

The pharmaceutical compositions according to this aspect of the present invention comprise about 0.1 to about 1000 micrograms of DNA. In some preferred embodiments, the pharmaceutical compositions contain about 1 to about 500 micrograms of DNA. In some preferred embodiments, the pharmaceutical compositions contain about 25 to about 250 micrograms of DNA. Most preferably, the pharmaceutical compositions contain about 100 micrograms DNA.

The pharmaceutical compositions according to this aspect of the present invention are formulated according to the mode of administration to be used. One having ordinary skill in the art can readily formulate a nucleic acid molecule that encodes vpr receptor protein. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline may be used. Stabilizers include gelatin and albumin.

The present invention relates to a method of treating an individual exposed to HIV by administering pharmaceutical compositions that comprise the vpr receptor protein or fragments thereof. Soluble fragments which bind to vpr are particularly useful.

Another aspect of the invention relates to methods of identifying compounds which inhibit vpr protein binding to vpr receptor protein. The methods comprise the steps of first contacting, in the presence of a test compound, vpr protein and vpr receptor protein and then determining the level of binding. Compounds which interfere with the binding of vpr to vpr receptor protein are useful to impede HIV replication; therefore such compounds will be useful as anti-HIV therapeutics alone or as part of a multi-faceted anti-HIV drug regimen which includes other therapeutics.

To practice these aspects of the invention, vpr protein and vpr receptor protein are contacted in the presence of a test compound. The level of binding of the proteins is determined. The resultant level of binding is compared to the known level of binding that occurs when both proteins are contacted with each other. In the absence of a compound that interferes with the binding, the two proteins will bind. As a control, vpr protein and vpr receptor protein are contacted in the absence of a test compound.

Test compound is provided, preferably in solution. Serial dilutions of test compounds may be used in a series of assays. Test compound may be added at concentrations from 0.01 µM to 1M. A preferred range of final concentrations of a test compound is from 1.0 µM to 100 µM.

Production of vpr protein is described in the U.S. Patent Application cited above which have been incorporated by reference. A preferred concentration range of the vpr used is about 1 µg/ml to 1 mg/ml. A preferred concentration of the vpr is about 50 µg/ml.

The vpr receptor protein may be produced by routine means using readily available starting materials following the teachings described herein. A preferred concentration range of the vpr receptor protein used is about 1 µg/ml to 1 mg/ml. A preferred concentration of the vpr receptor protein is about 50 µg/ml.

The means to detect whether or not vpr and vpr receptor protein are bound or if binding has been inhibited are routine and include enzyme assays and ELISA assays. One having ordinary skill in the art can detect protein binding using well known methods. One having ordinary skill in the art can readily appreciate the multitude of ways to practice a binding assay to detect compounds which modulate the binding of vpr to vpr receptor protein. For example, antibodies are useful for immunoassays which detect or quantitate vpr protein binding to vpr receptor protein. The immunoassay typically comprises incubating vpr protein and vpr receptor protein to allow protein-protein binding in the presence of a detectably labeled high affinity antibody capable of selectively binding to either vpr protein or vpr receptor protein, and detecting the labeled antibody which is bound to the protein. Various immunoassay procedures are described in *Immunoassays for the 80's*, A. Voller et al., Eds., University Park, 1981.

In this aspect of the invention, the antibody or either vpr protein or vpr receptor protein may be added to nitrocellulose, or other solid support which is capable of immobilizing proteins. The support may then be washed with suitable buffers followed by treatment with the detectably labeled vpr-specific antibody or the antibody that binds to the vpr receptor protein. The solid phase support may then be washed with the buffer a second time to remove unbound antibody. The amount of bound label on said solid support may then be detected by conventional means.

By "solid phase support" or "carrier" is intended any support capable of binding antigen or antibodies. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of antibodies may be determined according to well known methods. Those skilled in the art will be able to determine operative and optimal assay conditions for each determination by employing routine experimentation.

Positive control assays may be performed in which no test compound is added.

One of the ways in which the antibodies can be detectably labeled is by linking the same to an enzyme and use in an enzyme immunoassay (EIA), or enzyme-linked immunosorbent assay (ELISA). This enzyme, when subsequently exposed to its substrate, will react with the substrate generating a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, betagalactosidase, ribonuclease, urease, catalase, glucose-6-phosphate dehydrogenase, glucoamylase and acetylcholinesterase.

By radioactively labeling the antibody, it is possible to detect it through the use of a radioimmunoassay (RIA) (see, for example, Work, T. S., et al., *Laboratory Techniques and Biochemistry in Molecular Biology*, North Holland Publishing Company, N.Y., 1978. The radioactive isotope can be detected by such means as the use of a gamma counter or a scintillation counter or by autoradiography. Isotopes which are particularly useful for the purpose of the present invention are: $^{3}H$, $^{125}I$, $^{131}I$, $^{35}S$, $^{14}C$, and, preferably, $^{125}I$.

It is also possible to label the antibody with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence-emitting metals such as $^{152}Eu$, or others of the lanthanide series. These metals can be attached to the TNF-specific antibody using such metal chelating groups as diethylenetriaminepentaacetic acid (DTPA) or ethylenediamine-tetraacetic acid (EDTA).

The antibody also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isoluminol, theromaticacridiniumester, imidazole, acridinium salt and oxalate ester.

Likewise, a bioluminescent compound may be used to label the antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. Detection of the vpr-specific antibody or the antibody that binds to the vpr receptor protein may be accomplished by a scintillation counter, for example, if the detectable label is a radioactive gamma emitter, or by a fluorometer, for example, if the label is a fluorescent material.

In the case of an enzyme label, the detection can be accomplished by colorometric methods which employ a substrate for the enzyme. Detection may also be accomplished by visual comparison of the extent of enzymatic reaction of a substrate in comparison with similarly prepared standards.

As can be readily appreciated, one of the viral proteins may also be detectable and serve as a reporter molecule instead of or in addition to the antibody.

The components of the assay may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical and preferred immunometric assays include "forward" assays in which the antibody bound to the solid phase is first contacted with the one of the viral proteins to immobilize it. The second viral protein is added in the presence of the test compound. After a suitable incubation period, the solid support is washed to remove unbound protein. A second antibody is then added which is specific for the second viral protein. The second antibody is preferably detectable. After a second incubation period to permit the labeled antibody to complex with the second viral protein bound to the solid support through the unlabeled antibody and first viral protein, the solid support is washed a second time to remove the unreacted labeled antibody. This type of forward sandwich assay may be a simple "yes/no" assay to determine whether binding has occurred or may be made quantitative by comparing, the measure of labeled antibody with that obtained in a control. Such "two-site" or "sandwich" assays are described by Wide, *Radioimmune Assay Method*, Kirkham, Ed., E. & S. Livingstone, Edinburgh, 1970 pp. 199–206).

Other type of "sandwich" assays are the so-called "simultaneous" and "reverse" assays. A simultaneous assay involves a single incubation step wherein the antibody bound to the solid support and labeled antibody, both viral protein and the test compound are added at the same time. After the incubation is completed, the solid support is washed to remove uncomplexed proteins. The presence of labeled antibody associated with the solid support is then determined as it would be in a conventional "forward" sandwich assay.

In the "reverse" assay, stepwise addition first of a solution of labeled antibody to the viral proteins followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes may be used to construct a sensitive three-site immunoradiometric assay.

In some preferred embodiments, an anti-vpr antibody is fixed to a solid phase. vpr protein is contacted with the fixed antibody to form a complex. The complex is contacted with a vpr receptor protein in the presence of a test compound. Antibodies that, bind to the vpr receptor protein are then added. The solid phase is washed to removed unbound material. A control assay is performed in an identical manner except that no test compound is used. Detection of the antibodies that bind to the vpr receptor protein indicates that the vpr and vpr receptor proteins are capable of binding to each other in the presence of the test compound. Accordingly, failure to detect that antibodies that bind to vpr protein indicates that the test compound inhibits binding of vpr and vpr receptor proteins. Quantifying the level of binding in the presence and absence of test compound allows for the measurement of the extent of modulation that the test compound can cause on vpr binding to vpr receptor protein.

In some preferred embodiments, antibodies that bind to the vpr receptor protein are fixed to a solid phase. vpr receptor protein is contacted with the fixed antibody to form a complex. The complex is contacted with vpr protein in the presence of a test compound. Anti-vpr antibodies are then added. The solid phase is washed to removed unbound material. A control assay is performed in an identical manner except that no test compound is used. Detection of the antibodies that bind to vpr protein indicates that the vpr and vpr receptor proteins are capable of binding to each other in the presence of the test compound. Accordingly, failure to detect that antibodies that bind to vpr protein indicates that the test compound inhibits binding of vpr and vpr receptor proteins. Quantifying the level of binding in the presence and absence of test compound allows for the measurement of the extent of modulation that the test compound can cause on vpr binding to vpr receptor protein.

In the methods of identifying compounds that inhibit vpr protein binding to vpr receptor protein, fragments of vpr may be used provided the fragment used retains its ability to bind to the vpr receptor protein. Similarly, fragments of vpr receptor protein may be used provided the fragment used retains its ability to bind to vpr protein.

A further aspect of the present invention relates to kits for practicing the above described method of identifying compounds which inhibit vpr protein binding to vpr receptor protein. Kits according to this aspect of the invention comprises a first container comprising vpr protein, a second container comprising vpr receptor protein. Additionally, to practice the above defined method, means are required to distinguish vpr protein bound to the vpr receptor protein from unbound vpr protein or unbound vpr receptor protein. In a preferred embodiment of this aspect of the invention, a third container comprising an antibody that specifically binds to either the vpr protein or vpr receptor protein is provided. At least one of the contained components, preferably the antibody, may be conjugated with an agent, such as those described above, which allows its presence to be detected. In another preferred embodiment of this aspect of the invention, a fourth container is provided which contains an antibody that specifically binds to either the vpr protein or vpr receptor protein, but not the protein which is bound by the antibody in the third container. At least one of the contained components, preferably the antibody, may be conjugated with an agent, such as those described above, which allows its presence to be detected. In the kits of the invention which are useful to practice the methods of identifying compounds that inhibit vpr protein binding to a protein, fragments of vpr may be included provided the fragment used retains its ability to bind to the vpr receptor protein. Similarly, fragments of vpr receptor protein may be included provided the fragment used retains its ability to bind to vpr protein.

The present invention relates to antibodies that specifically bind to the human protein that has an apparent molecular weight of between 40–43 kD, that occurs in the cytoplasm of human cells, that binds to vpr and that is transported from the cytoplasm to the nucleus when bound to vpr. Production of such antibodies can be achieved by those having ordinary skill in the art without undue experimentation using readily available starting materials. The antibodies are useful in the assay to identify compounds that inhibit vpr binding to vpr receptor protein.

EXAMPLES

Example 1

Supernatants that contained vpr protein from insect cells infected with recombinant baculovirus that comprised a nucleotide sequence that encodes vpr were passed over a column. The column was washed with PBS. Cell lysates from U937 cells lysed in 100 mM NaCl, 50 mM Tris pH 8.0, 0.5% triton X-100 were then passed over the vpr loaded column and washed with PBS. The column was eluted with 100 mM triethanolamine, pH 11.5. The eluate was neutralized with 1M sodium phosphate, pH 6.8. Vpr and vpr receptor protein were coeluted as concluded from ELISA, SDS PAGE, silver stain or western blot.

vpr receptor protein was further purified by adding rabbit anti-vpr coated beads to the eluate. The beads are covalently bound to the antibody and the elution is done with the same triethanolamine solution described above. The beads are washed with PBS and eluted. The eluate is supplemented with equimolar amounts of gag p24. This solution is incubated at room temperature for 30 minutes. After incubation, beads coupled to a different anti-vpr antibody as well as antibody V7.8 are added to the solution. The supernatant is collected and contains greater than 90% pure vpr receptor protein which can be further purified by chromatography.

Example 2

Peptides that consist of vpr residues 27–39, 35–48, 41–55, 49–60 and 66–68 inhibit vpr/vpr receptor binding. Anti-vpr antibody binds to vpr peptide 41–60 inhibits vpr/vpr receptor binding.

Example 3

The following procedure was used to obtain substantially pure vpr receptor protein. Since the vpr receptor protein is Triton soluble, it can be purified from Triton soluble portions of cell lysates. The vpr receptor protein binds to vpr. Accordingly, using a column packed with vpr, the receptor protein can be isolated from Triton soluble portions of cell lysates and eluted as an isolated protein.

Recombinant vpr was produced in insect cells using baculovirus expression as described in Levy et al. (1994) *Proc. Natl. Acad. Sci. U.S.A.* 91:10873–10877, which is incorporated herein by reference. Recombinant vpr was purified by adding Triton X-100 at 0.05% v/v final concentration to the baculovirus supernatants. The supernatants were then passed through a rabbit anti-vpr column as described in Levy et al. (1994) *Proc. Natl. Acad. Sci. U.S.A.* 91:10873–10877 which was constructed in Harlow E. and E. Lane *Antibodies: A laboratory manual* Cold Spring Harbor Press, Cold Spring Harbor, N.Y. 1988, which is incorporated herein by reference. After extensive washing with PBS Triton X-100, the columns, the columns were eluted as follows. Three beds volumes of a pre-elution buffer at 10 mM Sodium Phosphate buffer plus Triton X-100 (0.05%), pH 8.0, were passed through the column, followed by the elution buffer consisting of 10 mM Triethanolamine plus 0.05% Triton X-100, pH 11.5. The eluate was collected in 0.5 ml aliquots and neutralized with 1/20 volume of 1M sodium phosphate buffer, pH 6.8 plus 0.05% Triton X-100.

A vpr-CNBr-Sepharose column was then constructed by coupling the purified recombinant vpr to cyanogen bromide activated sepharose beads (Sigma). Recombinant vpr at 1 mg/ml was incubated with swelled beads for 2 hours at 25 C in 10 mM $NaHCO_3$, 0.5M NaCl pH 8.3. The coupled beads were blocked with 1M glycine. Cell lysates are obtained using Triton X-100 at a final concentration of 0.05% v/v with about $10^7$ cells of one of the following types of cells: RD, U937, primary lymphocytes, primary monocytes or macrophages. The vpr-CNBr-Sepharose column is loaded with the lysates by letting the beads incubate with the lysates for at least one hour. Elution was performed using first pre-elution buffer composed of 10 mM Sodium Phosphate buffer pH 6.8, followed by elution buffer consisting of 100 mM glycine, pH 2.5. Elution fractions are neutralized with 1/20 volume of 1M sodium phosphate buffer, pH 8.0.

The eluate is isolated vpr. receptor protein which may be, visualized using silver stained SDS-PAGE where the vpr receptor runs at about 41 kD. The isolated vpr receptor protein binds to vpr as well as human glucocorticoid receptor (hGR) protein.

We claim:

1. Essentially pure viral protein R receptor protein characterized by a molecular weight of about 41 kD as determined using 12% SDS-PAGE, an ability to bind to viral protein R and solubility in Triton, or a fragment of said viral protein R receptor protein which binds to viral protein R.

2. The protein of claim 1 wherein said protein is characterized by a molecular weight of about 41 kD as determined using 12% SDS-PAGE, an ability to bind to viral protein R and solubility in Triton.

3. The protein of claim 1 wherein said protein is a fragment of the protein which has a molecular weight of about 41 kD as determined using 12% SDS-PAGE, said fragment having the ability to bind to viral protein R and solubility in Triton.

4. A method of identifying compounds which inhibit binding of viral protein R to the viral protein receptor protein of claim 1 which comprises the steps of:

a) contacting in the presence of a test compound, viral protein R protein or a fragment thereof and said viral protein R receptor protein or a fragment thereof, wherein in the absence of said test compound said viral protein R protein or said fragment thereof binds to said viral protein R receptor protein or said fragment thereof;

b) determining the level of binding and c) comparing that level to the level of binding that occurs when viral protein R protein and said viral protein R receptor protein are contacted in the absence of a test compound, wherein a decrease in binding levels in the presence of said test compound indicates that the test compound is a compound which inhibits binding of viral protein R protein to the viral protein R receptor protein of claim 1.

5. A kit for identifying compounds which inhibit binding of viral protein R protein to the viral protein R receptor protein of claim 1 which comprises a) a first container which contains viral protein R protein or a fragment thereof which binds viral protein R receptor protein or a fragment thereof, and b) a second container which contains said viral protein R receptor protein or a fragment thereof which binds viral protein R protein or a fragment thereof.

* * * * *